United States Patent [19]
Sherwood et al.

[11] Patent Number: 5,106,622
[45] Date of Patent: Apr. 21, 1992

[54] REPELLENT COMPOSITION CONTAINING NATURAL OILS OF CITRONELLA, CEDAR AND WINTERGREEN AND USE THEREOF

[76] Inventors: Karen Sherwood; Frank Sherwood, both of 31 Fisher Rd., Washington, N.J. 07882

[21] Appl. No.: 668,105

[22] Filed: Mar. 12, 1991

[51] Int. Cl.$^5$ .................. A61K 35/78; A01N 25/00
[52] U.S. Cl. .................. 424/195.1; 424/DIG. 10; 514/783
[58] Field of Search .............. 424/195.1, DIG. 10; 514/783

[56] References Cited

U.S. PATENT DOCUMENTS

| | | | |
|---|---|---|---|
| 173,945 | 2/1876 | Hall | 424/195.1 |
| 351,897 | 11/1886 | Boyer | 424/195.1 |
| 901,083 | 10/1908 | Ellis | 424/195.1 |
| 1,005,180 | 10/1911 | Ellis | 424/195.1 |
| 2,041,264 | 12/1931 | O'Kane | 424/DIG. 10 |
| 2,302,159 | 11/1942 | Wasum | 167/30 |
| 4,193,986 | 3/1980 | Cox | 424/195.1 |
| 4,320,112 | 3/1982 | Jones et al. | 424/19 |
| 4,671,960 | 6/1987 | Thielen et al. | 424/195.1 |
| 4,707,496 | 11/1987 | Simmons | 514/531 |
| 4,774,081 | 9/1988 | Flashanski | 424/78 |
| 4,774,082 | 9/1988 | Flashinski et al. | 424/78 |

OTHER PUBLICATIONS

The Merck Index 10th Ed. Merck & Co. Rahway, N.J. 1983 #6706.
Bishopp et al., J. Econ. Entomol. 18: 776, 777 (1925).
Parman et al., Technical Bulletin No. 80 U.S. Dept. of Agr. (Sep. 1928).
Drug and Cosmetic Industry 48(2): 149-151 (1941).
Hall et al., Insect Repellents and Attractants 5(9): 663 (1957).

*Primary Examiner*—Ronald W. Griffin
*Assistant Examiner*—Ralph Gitomer
*Attorney, Agent, or Firm*—Felfe & Lynch

[57] ABSTRACT

An environmentally safe, topical pest repellent is described. The repellent action is attributable to a mixture of natural oils of citronella, cedar, and wintergreen. These natural oils, mixed in equal amounts, are combined in a non-toxic base, such as olive oil. The mixture is effective against diverse species, including mosquitoes and ticks.

13 Claims, No Drawings ature has been developed.

REPELLENT COMPOSITION CONTAINING NATURAL OILS OF CITRONELLA, CEDAR AND WINTERGREEN AND USE THEREOF

FIELD OF THE INVENTION

This invention relates to compositions and methods for repelling pests, such as insects, arthopods (spiders, ticks, etc.), and other undesired non-human species. More specifically it relates to a repellent composition containing only naturally occurring ingredients.

BACKGROUND AND PRIOR ART

Repellents have been used for as long as history has been recorded, to prevent insects, arthropods, etc., from harming or annoying subject hosts such as humans, pets and other domesticated animals, and so forth. In addition, repellents have been used to prevent harm from pests such as insects and arthropods on inanimate materials, such as clothing, furniture, foodstuffs, etc. Examples of such materials are well known, including moth balls, and citronella candles. In the 20th century, very powerful, and very toxic chemicals have been developed which either repel or kill the aforementioned pests. Examples of these include "DDT" and "DEET". (Only acronyms are given, because these compounds are extremely well known to the artisan).

The noted toxicity of the aforementioned materials has been shown to not be restricted to the pests against which they are directed. Rachel Carson, in *Silent Spring*, documented the effect of DDT on the environment. Recently, DEET has been implicated as a toxin and potential carcinogen. Thus, there is an interest in safe, non-toxic chemicals which are also useful as pest repellents.

Safety to the user is not the only concern with respect to these repellents. As *Silent Spring* and other works have shown, repellents and other toxic chemicals persist in the environment for surprisingly long periods of time. Many repellents are used outdoors, generally in pristine areas which are not exposed to toxins. These persist, generally with harmful and damaging consequences. Further, those repellents which are toxic impact the natural ecosystems to which they are released, affecting complex, evolved systems of the native fauna. As an example of this, generally dragonflies are not considered an insect pest. They breed however, in wetlands which also habituate other insects, such as mosquitoes, which are considered pests. Application of a toxic repellent to ward off mosquitoes can also harm dragonflies, especially in the larvae, or nymph phase, where food is ingested in soluble form via gills. The resulting damage to the dragonfly population results in an increase in the population of their natural prey—including mosquitoes—which can lead to increases in the spread of diseases borne by the mosquitoes.

The foregoing example is just one of a number which could be cited to show the effect of pesticides and repellents on natural systems. Given the complex interrelationships that define nature, there is much that is unknown, and much that can be disturbed, sometimes permanently.

It is thus perhaps not surprising that there is interest in repellents which are not synthetics, and which may not be toxic.

An early example of a specific repellent, i.e., one directed against a particular type of insect, may be seen in U.S. Pat. No. 173,945, to Hall et al. This patent describes a moth repellent suitable for use on articles such as furs, woolen goods and pictures. The composition contains alcohol, turpentine, tar, camphor, mirbane essence (nitrobenzene), camphor spirits, citronella essence, bitter almond essence, and cedar extract. This liquid is brushed, or sprinkled on the area to be protected.

It will be understood from the disclosure that this composition is clearly unsuited for topical application to skin or other body areas of humans or domesticated animals, as many of the items are themselves toxic or noxious.

U.S. Pat. No. 351,897 is to the same effect in that it teaches a repellent composition suitable for application to paper. The composition contains tar, petroleum, oils of cedar, pennyroyal, sassafras and citronella, as well as creosole, carbolic acid, and sulphur. This composition is incorporated in, rather than applied to the paper, as it is added during the pulping process, or impregnated therein Bishopp et al., J. Econ. Entomol 18: 776 (1925) discusses the results of "test jar" experiments In these, a meat sample is coated with the material to be tested and is placed in a jar After a given period of time, the meat is studied for insect reaction. The reference states that some of the "essential oils", e.g., Oils culled from the essences of various plants and plant parts, show promise. Citronella, fennel, camphor (crude), clove bud oil and clove powder are mentioned.

In an extensive study, Parman et al., Technical Bulletin No. 80 (September 1928, U.S. Dept. of Agriculture) studied various substances to determine if they were effective against blow flies. The goal was to find prospective wound treating agents. In Table 9 of this reference, various essential oils were tested. Of 26 of these, three of the oils of the invention, i.e., citronella oil, pennyroyal oil, and camphor oil, were ranked 15th, 19th and 20th in terms of efficacy. Camphor oil, in fact, attracted insects of one species.

U.S. Pat. No. 2,041,264 describes various emulsions, one of which may contain citronella oil. Such emulsions are said to have insect repellent properties, although no empirical evidence supports this, at least in the cited patent.

By 1957, one sees a turning away from natural insecticides as Hall et al., Insect Repellents and Attractants 5(9): 663 (Sept. 1957) espouse the use of DDT and state that oil of citronella, pennyroyal, cedar, and camphor are "obsolete" because while they have a certain efficacy and limited repellency toward mosquitoes, this is "short lived". Indeed, this turning away from the essential oils is continued in U.S. Pat. No. 2,302,159, to Wasum, who says that citronella has a "strong unpleasant odor" and that some of the essential oils are annoying and possibly harmful against tender or sunburned skin.

In U.S. Pat. No. 4,193,986, a flea treatment composition is described. The vast majority of the composition (93-98%) is inert. The remaining, active fraction contains pennyroyal (10-40 parts), eucalyptus oil (5-20 parts), cedar oil (3-10 parts) citronella oil (5-10 parts), and oil of rue (1-2 parts). The preferred composition is 17-32 parts pennyroyal, 8-16 parts eucalyptus, 5-8 parts cedar, 5-8 parts citronella, and 1.25-1.75 parts rue. This material is designed for use on animals previously infected with fleas.

The ubiquitous citronella is used again in U.S. Pat. No. 4,320,112, where it is combined with naphthalene to form a pest repellent for garbage bags and the like.

U.S. Pat. No. 4,671,960 teaches a flea repellent. A collar device is taught and contains both plant solids (pennyroyal, eucalyptus, camomile), and small amounts of the oils of pennyroyal, eucalyptus and citronella.

This survey of the art shows that there is no teaching of the invention, which is a topical composition useful as a pest repellent, this composition comprising equal parts of the natural oils of citronella, cedar and wintergreen in a non-toxic carrier. It has been found, surprisingly in view of the art, that these compositions are effective when applied to human subjects. Further, by using an oil base, it has been found that a surprisingly large amount of effect ingredient, i.e., anywhere from 15-40 parts of the total composition, may be the active mixture. In tests in the field, the compositions of the invention not only performed effectively but did not aggravate the skin of subjects who were exposed to extremes of heat and humidity.

The invention is described in more detail in the description which follows.

DETAILED DESCRIPTION OF PREFERRED EMBODIMENTS

As described herein, the invention is a composition, suitable for use as a topical for humans, which has pest repellent properties. "Pest" as used herein is not limited to insects, as the material has been found to repel arthropods as well, such as ticks. A benefit of the composition is that it is a repellent, but is not toxic, so the various "pests", which are only pests when a host is introduced, are not themselves harmed.

The inventive compositions contain equal amounts of the natural oils of citronella, cedar and wintergreen. These natural oils are combined in a non-toxic, oil based carrier, such as oleic acids (i.e., olive oil).

"Natural" as a modifier of the word "oil" is an important descriptive. It is generally known that even under the most stringent conditions of purity, "natural" substances are not 100% uniform. In developing this invention, it was found that while every formulation of natural oils was effective, regardless of source, synthetic materials were not.

While citronella, cedar and wintergreen oils are required in the pest repellent compositions, they may also contain natural oil of pennyroyal.

The required oils comprise from about 15 to about 33 percent, or parts, of the entire composition, i.e., each oil is present in from about 5 to about 11 parts of the total composition. When pennyroyal oil is added, the amounts of the three can be reduced. Additionally, natural oils of eucalyptus and camphor can be added, in small amounts.

In a particularly preferred embodiments, and the one used in the experiments which follow, the constituents of the repellent composition are as follows:

| | |
|---|---|
| Citronella | 6.9 parts |
| Cedar | 6.9 parts |
| Wintergreen | 6.9 parts |
| Pennyroyal | 10.3 parts |
| Olive oil | 69.0 parts |
| Composition | 100 parts |

All materials are readily available from, e.g., health food stores, and formulation of the compositions simply involves mixing the recited oils together.

A composition in accordance with the above formulation was tested in the following case studies.

CASE STUDIES—TEST 1

A group of fifteen volunteers applied the composition described above during a wilderness trek in the Midwest, during which time the activities included mountain climbing, wilderness walking, etc. The subjects were asked to record what insects they observed. While responses varied, nearly all reported chiggers, horseflies, blackflies, ticks, and mosquitoes. Some also reported wasps, horseflies, fleas and gnats. These descriptions are consistent with insect populations in the Oklahoma Flatlands, which is where the test took place. The subjects were asked to apply the composition to the exposed parts of their bodies—arms, legs, face, etc., in the morning before the day's activities, and in the evening before retiring. Some also applied it at midday as well. Approximately half of the respondents reported that they experienced no insect bites or stings. Two subjects reported a few ticks, but only one received any tick bites. The efficacy of the composition was good for about 7 hours, at which time a second application was desirable.

CASE STUDIES—TEST 2

A study was carried out in May, 1990 over an approximately two week period. Six volunteers, travelling in the New Jersey Pine Barrens observed heavy populations of ticks, mosquitoes, and blackflies. The composition referred to supra was applied 2-4 times a day. The volunteers experienced no mosquito bites and there were reports of observing ticks lighting on exposed but protected skin, and leaving without biting or attachment. In addition, volunteer subjects reported that exposed areas which had not been protected were bitten by mosquitoes and other insects.

CASE STUDIES—TEST 3

A test was carried out in Eastern Kansas, at a National Wildlife refuge. At the time of the test, the area was experiencing heavy infestation of "flood mosquitoes", which are a large, and aggressive variety.

The composition was applied anywhere from 1-4 times a day, and no bites from mosquitoes were reported. In addition, it was observed that chigger bites were experienced on unprotected skin at night.

CASE STUDIES—TEST 4

Smaller group of volunteers tested formulations in South Central Pennsylvania, the Eastern region of North Carolina, Maine, and the Virginia coastal marshes. Gnats, biting flies, ticks, mosquitoes, horseflies, and blackflies were observed, although all insects were observed in all areas. The volunteers applied the formulation once, and found that this was generally sufficient to repel the insects and ticks.

The foregoing case studies show that the composition described herein is generally effective against all insects present as well as arthropod fleas and ticks. In nearly every case, the subjects were completely satisfied with the product, which either eliminated or drastically reduced the frequency of insect and tick attack.

Thus, the compositions described above are useful as topicals for repelling pests, such as insects and ticks.

The fact that it is effective on humans would had the skilled artisan to conclude that efficacy would be expected with domestic animals, including pets. Hence, a method for repelling pests is taught, wherein the above compositions are used by applying them to the exposed skin or other areas of the body. "Other areas" includes, e.g., hair, foot soles, and unexposed body parts.

As efficacy on a living subject is less predictable than is efficacy on inanimate material, the foregoing results suggest that the composition is also effective as a repellent for inanimate material, such as clothing, furniture, and so forth. In addition, it suggests that the material may be effective as an environmental repellent, when used in the form of a fogger, non-aerosol spray, and so forth.

The material can be used in the oil based form, described supra. and also as a cream, lotion, spray, roll-on, or other conventional form of repellent. These need not be described herein, as they are readily known to the skilled artisan.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. Composition useful as a topical pest repellent comprising an equal amount ranging from about 5 parts to about 11 percent by weight of said total composition of each of natural oil of citronella, natural cedar oil, and natural oil of wintergreen in a non-toxic carrier.

2. Composition of claim further comprising natural oil of pennyroyal.

3. Composition of claim 1, wherein said non toxic carrier comprises oleic acid.

4. Composition of claim 1, wherein said composition is in the form of a liquid.

5. Composition of claim 1, wherein said composition is in the form of a cream.

6. Composition of claim 1, wherein said composition is in the form of a non-aerosol spray.

7. Composition of claim 1, wherein said composition is in the form of a fogger.

8. Composition of claim 2, comprising about 6.9 parts by weight of each of said natural oil of citronella, said natural oil of wintergreen, about 10.3 parts by weight of natural oil of pennyroyal, and about 69 parts by weight of said non-toxic carrier.

9. Method for repelling pests comprising from a subject comprising topically applying to said subject an amount of the composition of claim 1 effective to repel said pest.

10. Method for repelling pests from an area comprising distributing the composition of claim 1 in an amount sufficient to repel pests therefrom.

11. Method of claim 9, wherein said subject is a human.

12. Method of claim 9, wherein said subject is a domesticated animal.

13. Method of claim 10, wherein said area is habituated.

* * * * *